US009089854B1

(12) United States Patent
Stutts

(10) Patent No.: US 9,089,854 B1

(45) Date of Patent: Jul. 28, 2015

(54) METHOD AND SYSTEM FOR ATOMIZED DISPERSION OF HYDROGEN SULFIDE SCAVENGER

(76) Inventor: Tommy Stutts, Athens, TX (US)

( * ) Notice: Subject to any disclaimer, the term of this patent is extended or adjusted under 35 U.S.C. 154(b) by 917 days.

(21) Appl. No.: 13/099,344

(22) Filed: May 2, 2011

Related U.S. Application Data

(60) Provisional application No. 61/329,978, filed on Apr. 30, 2010, provisional application No. 61/424,694, filed on Dec. 20, 2010.

(51) Int. Cl.

| | |
|---|---|
| ***B05B 17/00*** | (2006.01) |
| ***B05B 1/00*** | (2006.01) |
| ***B05B 9/043*** | (2006.01) |
| ***B05B 12/02*** | (2006.01) |
| ***B05B 3/02*** | (2006.01) |
| ***B05B 12/10*** | (2006.01) |
| ***B05B 3/10*** | (2006.01) |
| ***B05B 3/04*** | (2006.01) |
| ***A01G 25/16*** | (2006.01) |
| ***A01G 13/06*** | (2006.01) |
| ***A01G 15/00*** | (2006.01) |
| ***A62C 3/00*** | (2006.01) |
| ***E21B 35/00*** | (2006.01) |
| ***E01H 13/00*** | (2006.01) |
| ***A62C 35/00*** | (2006.01) |
| ***A61M 11/06*** | (2006.01) |

(52) U.S. Cl.

CPC ................ *B05B 1/00* (2013.01); *A01G 13/065* (2013.01); *A01G 15/00* (2013.01); *A01G 25/16* (2013.01); *A01G 25/165* (2013.01); *A61M 11/06* (2013.01); *A62C 3/00* (2013.01); *A62C 35/00* (2013.01); *B05B 3/02* (2013.01); *B05B 3/0486* (2013.01); *B05B 3/1007* (2013.01); *B05B 3/1014* (2013.01); *B05B 9/043* (2013.01); *B05B 12/02* (2013.01); *B05B 12/10* (2013.01); *E01H 13/00* (2013.01); *E21B 35/00* (2013.01); *Y02B 30/545* (2013.01)

(58) Field of Classification Search

CPC ........ B05B 12/02; B05B 12/10; B05B 3/105; B05B 3/02; B05B 3/0486; B05B 3/1007; B05B 3/1064; B05B 5/0407; B05B 3/1014; B05B 15/00; B05B 7/2408; B05B 7/2478; B05B 7/0012; B05B 9/043; A01G 15/00; A01G 13/065; A01G 25/16; A01G 25/165; E01H 13/00; A01M 7/0014; E21B 35/00; E21B 37/00; E21B 41/02; E21B 37/06; A62C 3/00; A62C 35/00; Y02B 30/545; A61M 11/06; B01F 3/04049

USPC ............. 239/1, 2.1, 14.1, 69, 70, 75, 77, 214, 239/215, 222.11, 222.13, 222.15, 223, 224, 239/289, 302, 379, 373, 222.17; 261/28, 261/78.2; 169/69; 166/312, 902

See application file for complete search history.

(56) References Cited

U.S. PATENT DOCUMENTS

| | | | | | |
|---|---|---|---|---|---|
| 1,586,997 | A | * | 6/1926 | Hull | 239/77 |
| 2,945,627 | A | * | 7/1960 | McDermott | 239/215 |
| 3,004,403 | A | * | 10/1961 | Laporte | 239/223 |

*Primary Examiner* — Steven J Ganey

(74) *Attorney, Agent, or Firm* — Rick B. Yeager

(57) ABSTRACT

A method and system for the atomized dispersion of a liquid composition using one or more electrically or hydraulically driven fans with atomizers. In one example, air flow from a plurality of fans, each in proximity to an atomizer driven by an overdrive unit at 2-10 times the fan speed, provides an efficient dispersion 30-50 micron droplets of a scavenger in order to effectively suppress hydrogen sulfide in an area such as an oil well. The system provides a rapid response when $H_2S$ exceeds a threshold concentration. The fans deliver atomized scavenger over a relatively large area, so that the scavenger can tie-up or neutralize large amounts of $H_2S$ very quickly.

15 Claims, 4 Drawing Sheets

METHOD AND SYSTEM FOR ATOMIZED DISPERSION OF HYDROGEN SULFIDE SCAVENGER

RELATED APPLICATIONS

This is a provisional patent application. This U.S. non-provisional patent application is related to U.S. Provisional Patent Application No. 61/329,978 filed by applicant on Apr. 30, 2010 and claims the priority date of that application. This application is also related to U.S. Provisional Patent Application No. 61/424,694 filed by applicant on Dec. 20, 2010.

BACKGROUND

1. Field of Invention

The current invention relates to a method and system for the atomized dispersion of a liquid composition. In one embodiment, the system disperses a hydrogen sulfide scavenger, such as in proximity to an oil well.

2. Prior Art

The prior art includes numerous examples of hydrogen sulfide ($H_2S$) scavenging products. Some of these products are designed for "dry" processes to remove the gas from environments outside of a well, and others are "wet" processes such as applying the scavenger material as an additive to drilling mud.

These approaches are not well suited to situations where hydrogen sulfide may be encountered in surges. For instance, in the wet processes a scavenger material is typically added to mud in an amount necessary to offset an expected amount of $H_2S$. Thus if the gas is encountered in a higher concentration, the scavenger is unable to neutralize all of the gas. On the other hand, if extra scavenger is used at all times, then it represents a waste of the scavenger and a large extra expense.

There is a need for improved safety systems for $H_2S$ exposure from oil wells and other environments. In particular, there is a need to provide improved systems and methods for drilling operations in order to have time to safely evacuate personnel in the event of an $H_2S$ incident.

Nozzle plugging is a common failure of prior art liquid composition delivery systems such as hydrogen sulfide ($H_2S$) scavenging compositions, fire foam, and odor treatment. One aspect of the current invention is to provide a reliable atomization and dispersal of a liquid composition over an area with an atomizer that will not clog due to its design, flow, and materials of construction.

SUMMARY

One aspect of the current invention is the use of one or more fans in combination with sensors, controllers, and atomizing equipment to deliver an atomized scavenger material over an area in rapid response to a situation where $H_2S$ exceeds a threshold concentration.

In one embodiment, an overdrive unit is provided to drive an atomizer at 2-10 times the fan speed for more efficient atomization of a liquid composition.

The fans deliver atomized scavenger effectively over a relatively large area, so that the scavenger can tie-up or neutralize large amounts of $H_2S$ very quickly.

One use of the current invention is to permit time for personnel evacuation from an area in the event of an $H_2S$ exposure incident.

DESCRIPTION OF EMBODIMENT

Scavenger Atomization in Vicinity of an Oil Well Head

Figure 1:
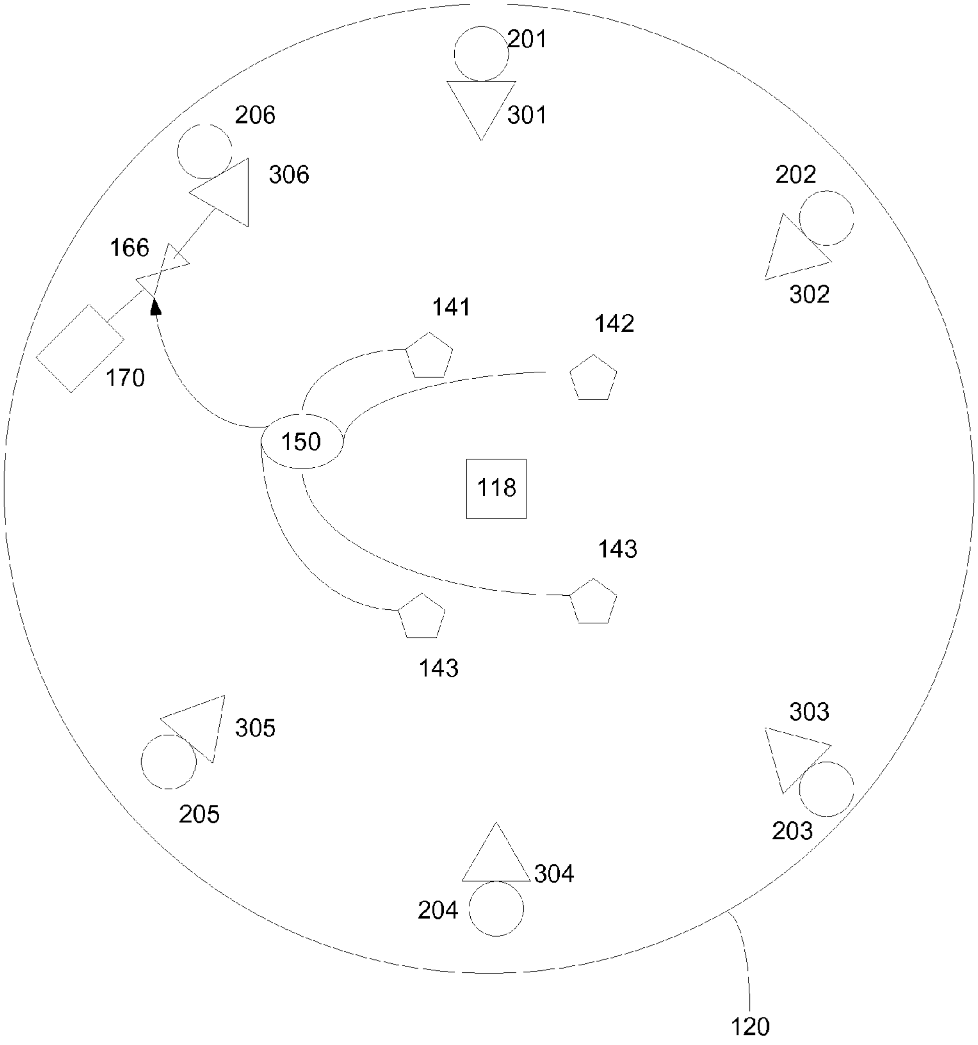
FIG. 1 is a schematic representing an example application of the current invention with six fans and atomizers serving a exposure area.

FIG. 1 is a schematic which shows one example of the current invention. In this example, six fans 201, 202, 203, 204, 205, and 206 are provided in exposure area 120 in the proximity of an oil well 118. In other examples, various numbers of fans may be used for various sizes of exposure or distribution areas around oil wells, storage tanks, pipelines, or other sources of hydrogen sulfide. In this example, each fan may be electrically or hydraulically driven. Typically, one to twenty fans are used.

In this example, at least one atomizer 300 is provided for each fan as described below.

In this example, one or more sensor 140 is provided to detect the presence of $H_2S$. When the gas is present above a threshold level, a controller 150 opens a valve 160 to permit a scavenger 400 to flow into the atomizer. In this example, the scavenger is held in a tank 170, and is delivered to the atomizer by a pump 180 which is driven by the fan motor as described below. In other examples, other scavenger delivery systems may be provided.

Fans

Figure 2:
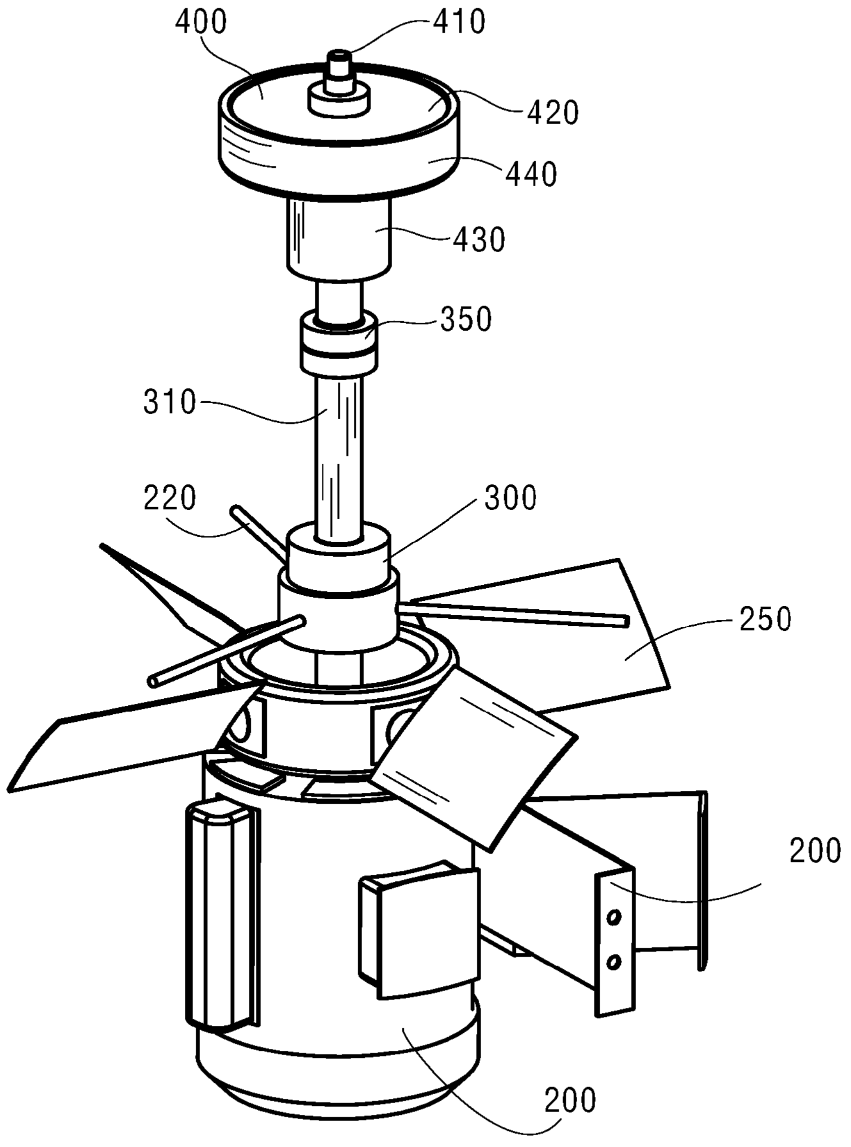
FIG. 2 is a side view of a fan with a scavenger atomization unit attached.

FIG. 2 is a side perspective view of an example fan 250 and atomization head 400. In this example, the fan is driven by a motor 200 which is supported in a housing (not shown) by supports 210. Various sizes and makes of fans may be used.

In one example, the fan is hydraulic driven to reduce the risk of explosion. The fan may have a high safety rating. In other examples, electric motors may drive the fans.

Atomizer

Figure 3:
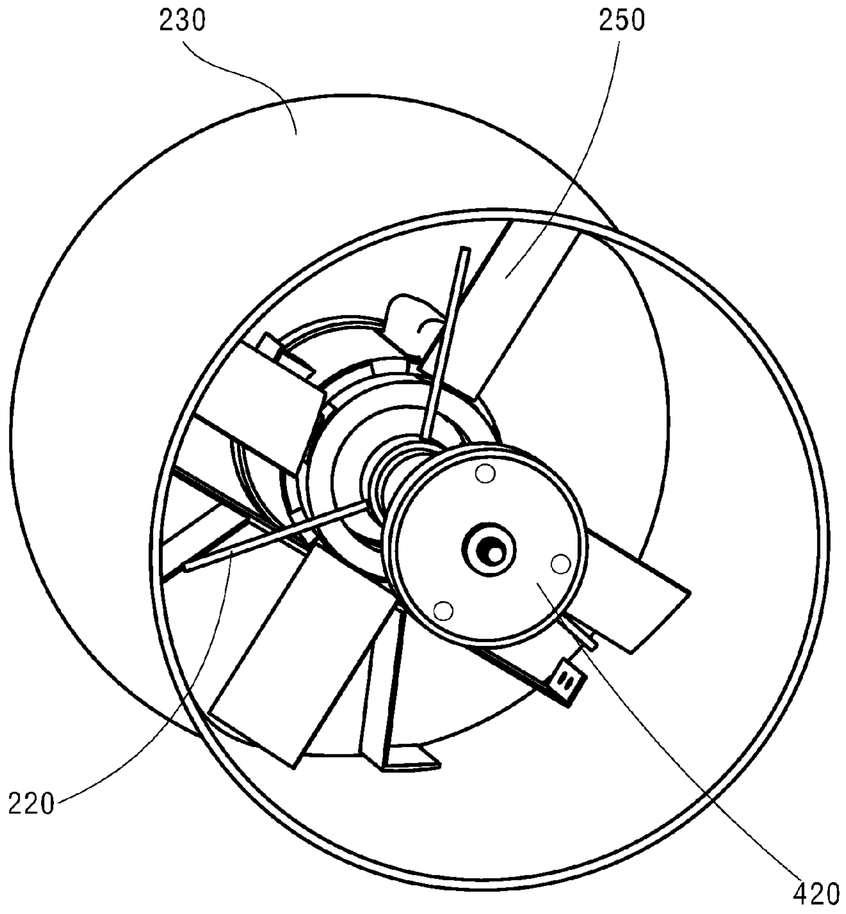
FIG. 3 is a detailed front view of the atomization unit of FIG. 2.
Figure 4:
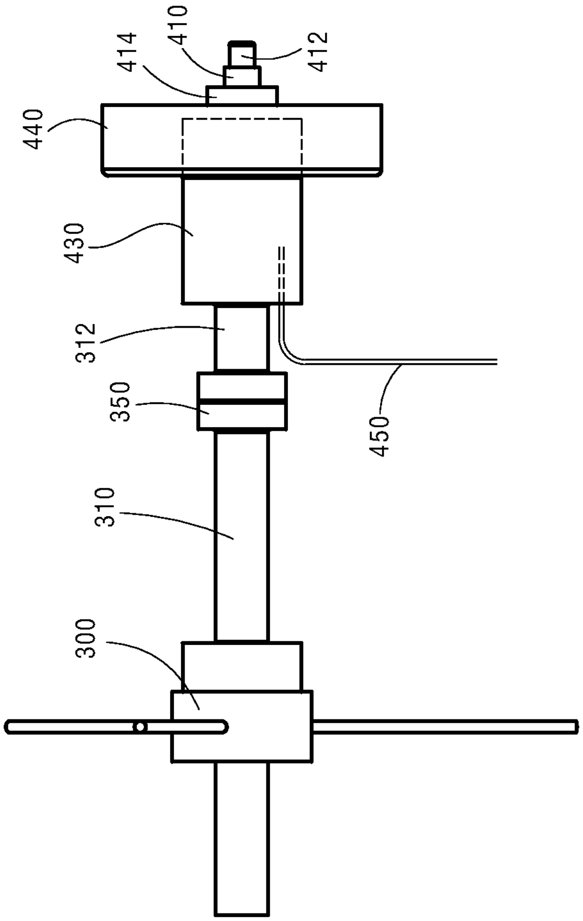
FIG. 4 is a detailed side view of the atomization unit of FIG. 2.

In FIGS. 2, 3, and 4, an atomizer comprises an overdrive unit 300 attached to the front of the fan. The overdrive unit 300 drives an interchangeable atomization head 400 with shaft 312 which is attached to shaft 310 with a coupler 350. In this example, the atomizer is driven by the fan and the motor itself. Supports 220 permit centering and support of the overdrive unit with respect to a housing 230. In general the droplet size of the liquid composition is related to diameter of the atomization head and the rotation speed of the atomization head.

In this example, a fluid hub 430 is provided to supply liquid to the atomizer head. There is a gap between the fluid hub 430 and the shaft 312 so that a liquid composition may be delivered with a ⅜ inch to ⅝ inch delivery line (not shown) to the proximity of the atomizer head. An air gap is provided between the end of the delivery line and the atomizer head. An end plate 420 is secure to the atomizer head 440 and shaft 412 with nut 410 and flat washer 414. A circumferential gap is provided between the end plate and the atomizer head 440. A mesh or grating is typically attached to the end plate so that is covers the gap.

The liquid composition delivery line 450 may be secured to the fan housing 230. In some examples, the delivery line is connected to a liquid composition reservoir and pump. In other examples, the reservoir may be located above the fan so that the liquid is gravity fed through the feeder tube delivery line.

In this example, the atomizer is where a breakdown of the "scavenger" $H_2S$ suppressant is distributed with a typical particle size of 30-50 micron droplets. The air flow from the fans provides an efficient dispersion of the scavenger in order to effectively suppress the $H_2S$.

FIG. 3 is a detailed view of the atomization unit of FIG. 2.

Over-Drive Box

In one embodiment, an overdrive unit is provided to spin the atomization head at a rate that is 2-10 times faster than the motor and fan speed. Fan speeds are typically provided in speeds of 750, 1250, 1750, or 3150 rpm. It is generally desirable to rotate the atomizer at speeds greater than the fan speed.

The selection of factors such as fan speed, overdrive speed, atomizer head diameter permits flexibility is adapting the system to various liquid compositions. For instance, higher overdrive speeds and greater diameters of atomization heads provide reduced droplet size for treatment of a larger area.

Scavenger

A scavenger is a molecule that ties up or neutralizes hydrogen sulfide. In this example, a prior art $H_2S$ neutralizer is used. This product was designed to be an additive to drilling mud, and has a high viscosity. Although the product is very effective at tying up $H_2S$, it is not generally practical to apply the material to the air around an oil well.

Sensors

Referring again to FIG. 1, in this example, four sensors 141, 142, 143, and 144 are distributed around the exposure area 120. In other examples, the sensors may be mounted with the fans. The sensors may be any sensor that can detect the gas. In this example, the sensors can detect the presence of the gas very quickly, and the controller 150 sends a signal to open valve 160 and to begin pumping scavenger material to the atomizer.

Control

In one example, sensors are provided to detect the escape of $H_2S$, and the system triggers a valve at each fan location to quickly distribute the scavenger in micron-scale droplets that attach to the hydrogen sulfide molecule and neutralize its harmful effect. This response is typically within 2-5 seconds of detection. The fast response and efficient dispersal of scavenger permits workers time to exit from an exposure area around an oil rig well; and to return more quickly.

In other examples, the potential "exposure area" may be a refinery or pipeline or other oil and gas processing area. Other potential non-oil and gas applications are described below.

Although the prior art includes various $H_2S$, the delivery of those scavengers has not been as efficient as the current invention. One factor in the slow response of prior art scavenger methods has been the high viscosity of the scavenger. For instance, the high viscosity can tend to plug a nozzle, so an atomizing head permits a more reliable delivery.

The system can shut down when $H_2S$ or other materials are below threshhold limits. This fast response reduces waste of scavenger.

Since $H_2S$ is about 18% denser than air, it can be treated more effectively by delivering and distributing scavenger above a source. In some examples, the amount of scavenger and the air flow can be controlled as appropriate based on terrain, wind direction, and other factors. For example, in a high wind, the system in FIG. 1 may use only the upwind fan locations; or the downwind fans may be set to a higher air flow than the upwind fans. Thus the ability to control air flow and scavenger flow offers a more precise way to get dispersant to an exposure area where it is in a useful form to quickly tie up $H_2S$. By contrast, a prior art method of mixing a scavenger with drilling mud is less efficient. In that case, scavenger is added in hope that it will bond to $H_2S$, but large volumes of gas may not have efficient contact with the mud.

Example

In one example, the fan blade pitch is in the range of 10-75%; the fan blades are in the range of 6-60 inches; and are driven by a ⅛ hp to 30 hp motor. A gear ratio in the range of 1:1 to 10:1 may be used, and an overdrive capability may be provided.

The housing for the atomizer gear box may be fabricated from a variety of materials including plastic, wood, or stainless steel. In this example, the scavenger flow rate is about 0.1 to 50 gallons per minute.

The system may be fabricated to comply with a range of safety ratings from standard to Class I-Div I.

Scavenger Atomization in Vicinity of a Pipeline

In this example, one or more detection and distribution stations are positioned along key locations on a pipeline.

Other "Scavengers"

In other examples the "scavenger" $H_2S$ suppressant is replaced with fire foam; fire fighting agents; odor suppressants; liquid fertilizer dispersants; defoliation agents; or any other chemical agent dispersant.

In one example, portable trailer mounted systems are provided for fire fighting. In another example, fire suppressant systems are permanently provided in high risk areas where flammable materials are used or processed. In one application, firefighting with foam injection and efficient dispersal can substantially improve the effectiveness of fire control.

In various examples, the system may be provided for oil and gas rigs; fire control; sanitation; and other applications. In some applications, high performance mitigation of dust or odor may be obtained. In other examples, the aerial application of a herbicide or other agricultural agents is provided with high performance.

A cylindrical housing may be provided in a range of thickness including 14 ga. to ½ inch steel, aluminum, ABS, composites, carbon finer, plastic, fiberglass or other materials.

The power may be provided by steam, hydraulic, pneumatic, solar, electrical, wind, or other source. In some applications, a Class 1 Division 1 or 2 safety rating can be obtained without compromising efficiency.

In some applications, heating or cooling can be provided to improve material flow or efficiency.

Hand Sprayers

In this embodiment, the "scavenger" may be provided with a hand sprayer.

Device Mounting

In various examples, the fan and other components may be mounted on trailers; on vehicle frames; on ground structures; on tower structures; or may be portable.

Activation Methods

In various examples, the system may be manually activated; timer-based; chemical sensor-based; heat or temperature activated; or by other control methods.

The scope of the current invention is not limited to the specific embodiments and examples described above.

What is claimed is:

1. A device for the atomized dispersion of a liquid composition, the device comprising a fan mounted on a housing, the fan oriented to blow air away from the housing;

a fan power source;

a hydrogen sulfide sensor;

a controller in communication with the sensor;

a liquid composition reservoir holding a volume of the liquid composition;

an overdrive unit;

an atomizer in proximity to the fan, the atomizer driven by the overdrive unit, such that the fan disperses atomized liquid composition; and a liquid composition delivery line from the liquid composition from the reservoir to the atomizer.

2. The device of claim 1 wherein the liquid composition comprises a hydrogen sulfide scavenger.

3. The device of claim 1 further comprising a control valve in communication with the controller.

4. The device of claim 1 wherein the fan power source is selected from the group comprising steam, hydraulic, pneumatic, solar, electrical, and wind.

5. The device of claim 1 wherein the fan power source is a fan motor; and a liquid composition pump is driven by the fan motor.

6. The device of claim 1 wherein the fan housing is selected from the group comprising a ground structure, a tower structure, a portable frame, a trailer, and a vehicle frame.

7. The device of claim 1 wherein the liquid composition reservoir, a liquid composition pump, and the atomizer are provided as a hand sprayer.

8. A system for the controlled atomized dispersion of a liquid composition to an area, the system comprising at least one liquid composition reservoir holding a volume of the liquid composition;

a plurality of fans positioned in the area, each fan comprising a fan housing, a fan power source, an overdrive unit, an atomizer in proximity to each fan, such that the fan disperses atomized liquid composition, and at least one liquid composition delivery line from the liquid composition reservoir to the atomizer;

at least one sensor; and at least one controller in communication with the sensor.

9. The system of claim 8 wherein the liquid composition comprises a hydrogen sulfide scavenger; and the at least one sensor is a hydrogen sulfide sensor.

10. The system of claim 9 wherein a plurality of hydrogen sulfide sensors are positioned in the area.

11. The system of claim 8 wherein the liquid composition is selected from the group comprising fire foam, a fire fighting agent, an odor suppressant, a liquid fertilizer dispersant, and a defoliation agent.

12. The system of claim 9 wherein the fan power sources are fan motors; and liquid composition pumps are driven by the fan motors.

13. A method for the controlled atomized dispersion of a liquid composition to an area, the method comprising positioning a plurality of fans in the area, each fan comprising a fan housing, a fan power source, a liquid composition reservoir holding a volume of the liquid composition, an overdrive unit, an atomizer in proximity to the fan, and a liquid composition delivery line from the liquid composition reservoir to the atomizer, and a controller;

providing at least one sensor in the area; and providing a signal from the sensor to the controllers to cause the liquid composition to be delivered to the atomizers, so that each fan distributes atomized liquid composition in over a portion of the area.

14. The method of claim 13 wherein the liquid composition comprises a hydrogen sulfide scavenger; and the sensor is a hydrogen sulfide sensor.

15. The method of claim 13 wherein the liquid composition is selected from the group comprising fire foam, a fire fighting agent, an odor suppressant, a liquid fertilizer dispersant, and a defoliation agent.

* * * * *